US011439994B2

(12) United States Patent
Dubreuil et al.

(10) Patent No.: US 11,439,994 B2
(45) Date of Patent: Sep. 13, 2022

(54) METHOD FOR THE HYDROGENATION OF AROMATICS USING A NICKEL-BASED CATALYST

(71) Applicant: IFP Energies Nouvelles, Rueil-Malmaison (FR)

(72) Inventors: Anne-Claire Dubreuil, Lyons (FR); Agathe Martel, Lyons (FR)

(73) Assignee: IFP Energies Nouvelles, Rueil-Malmaison (FR)

(*) Notice: Subject to any disclaimer, the term of this patent is extended or adjusted under 35 U.S.C. 154(b) by 0 days.

(21) Appl. No.: 17/074,871

(22) Filed: Oct. 20, 2020

(65) Prior Publication Data
US 2021/0031179 A1 Feb. 4, 2021

Related U.S. Application Data

(63) Continuation of application No. 16/472,381, filed as application No. PCT/EP2017/082024 on Dec. 8, 2017, now abandoned.

(30) Foreign Application Priority Data

Dec. 22, 2016 (FR) ..................... 1663093

(51) Int. Cl.
| | | |
|---|---|---|
| *B01J 37/02* | (2006.01) |
| *B01J 21/04* | (2006.01) |
| *B01J 23/755* | (2006.01) |
| *C07C 5/10* | (2006.01) |
| *C10G 45/48* | (2006.01) |
| *B01J 35/00* | (2006.01) |
| *B01J 37/08* | (2006.01) |

(52) U.S. Cl.
CPC .......... *B01J 37/0203* (2013.01); *B01J 21/04* (2013.01); *B01J 23/755* (2013.01); *B01J 35/006* (2013.01); *B01J 37/0205* (2013.01); *B01J 37/0236* (2013.01); *B01J 37/08* (2013.01); *C07C 5/10* (2013.01); *C10G 45/48* (2013.01); *C07C 2521/04* (2013.01); *C07C 2523/755* (2013.01); *C10G 2300/1096* (2013.01); *C10G 2300/70* (2013.01)

(58) Field of Classification Search
CPC .......... C10G 45/48; C10G 45/46; C07C 5/10; C07C 5/02
See application file for complete search history.

(56) References Cited

U.S. PATENT DOCUMENTS

| | | | | |
|---|---|---|---|---|
| 5,457,252 | A | * | 10/1995 | Gill .......................... C07C 5/10 208/143 |
| 5,736,484 | A | | 4/1998 | Polanek et al. |
| 10,307,738 | B2 | | 6/2019 | Boualleg et al. |
| 2006/0149097 | A1 | | 7/2006 | Soled et al. |

FOREIGN PATENT DOCUMENTS

| | | | | |
|---|---|---|---|---|
| FR | 2984761 | B1 | 12/2014 | |
| WO | 13093231 | A1 | 6/2013 | |
| WO | WO-2013093231 | A1 * | 6/2013 | ............. C07C 11/02 |
| WO | 16037830 | A1 | 3/2016 | |

OTHER PUBLICATIONS

WO2013/093231A1_EnglishTranslation (Year: 2013).*
International Search Report PCT/EP2017/082024 dated Mar. 6, 2018 (pp. 1-2).

* cited by examiner

*Primary Examiner* — Youngsul Jeong
(74) *Attorney, Agent, or Firm* — Millen, White, Zelano and Branigan, P.C.; Harry B. Shubin

(57) ABSTRACT

Hydrogenation of at least one aromatic or polyaromatic compound contained in a hydrocarbon feedstock having a final boiling point below or equal to 650° C., at a temperature of between 30 and 350° C., at a pressure of between 0.1 and 20 MPa, at a hydrogen/(aromatic compounds to be hydrogenated) molar ratio between 0.1 and 10 and at an hourly space velocity HSV of between 0.05 and 50 h$^{-1}$, in the presence of a catalyst comprising an alumina support and an active phase comprising nickel, prepared by
  i) contacting the support with a solution containing a nickel precursor;
  ii) bringing the support into contact with a solution containing an organic compound comprising a carboxylic acid, or alcohol, or ester, or amide function;
  iii) drying the impregnated support at a temperature below 250° C.;
  i) and ii) being carried out separately, in any order, or at the same time.

14 Claims, No Drawings

METHOD FOR THE HYDROGENATION OF AROMATICS USING A NICKEL-BASED CATALYST

FIELD OF THE INVENTION

The invention relates to a process for the hydrogenation of at least one aromatic or polyaromatic compound contained in a hydrocarbon feedstock, in the presence of a nickel-based catalyst supported on an alumina support prepared using an organic additive, enabling the transformation of the aromatic compounds of petroleum or petrochemical cuts by conversion of the aromatic rings into naphthenic rings.

PRIOR ART

The catalysts for the hydrogenation of aromatic compounds are generally based on metals from Group VIII of the Periodic Table of the Elements, such as nickel. The metal is in the form of nanoscale metal particles deposited on a support which may be a refractory oxide. The content of metal from Group VIII, the optional presence of a second metal element, the size of the metal particles, the distribution of the active phase in the support and also the nature and the pore distribution of the support are parameters which may have an influence on the performance of the catalysts.

The rate of the hydrogenation reaction is governed by several criteria, such as the diffusion of the reactants toward the surface of the catalyst (external diffusional limitations), the diffusion of the reactants in the porosity of the support toward the active sites (internal diffusional limitations) and the intrinsic properties of the active phase, such as the size of the metal particles and the distribution of the active phase within the support.

As regards the size of the metal particles, it is generally accepted that the catalyst becomes more active as the size of the metal particles decreases. Furthermore, it is important to obtain a particle size distribution which is centred on the optimum value and also a narrow distribution around this value.

For the purpose of obtaining better catalytic performance, in particular a better selectivity and/or activity, it is known in the prior art to use additives of organic compound type for the preparation of metal catalysts for the hydrogenation of aromatics.

For example, application FR 2 984 761 discloses a process for the preparation of a selective hydrogenation catalyst comprising a support and an active phase comprising a metal from Group VIII, said catalyst being prepared by a process comprising a step of impregnation with a solution containing a precursor of the metal from Group VIII and an organic additive, more particularly an organic compound having from one to three carboxylic acid functions, a step of drying the impregnated support and a step of calcining the dried support in order to obtain the catalyst.

Document US 2006/0149097 discloses a process for the hydrogenation of aromatic compounds of benzenepolycarboxylic acid type in the presence of a catalyst comprising an active phase comprising at least one metal from Group VIII, which catalyst is prepared by a process comprising a step of impregnation with a solution containing a precursor of the metal from Group VIII and a step of impregnation with an organic additive of amine or amino acid type. The step of impregnation with the organic additive can be carried out before or after the step of impregnation with the active phase, or even simultaneously.

Within this context, one of the objectives of the present invention is to provide a process for the hydrogenation of aromatic or polyaromatic compounds in the presence of a supported catalyst having a nickel active phase, prepared using particular organic compounds enabling a performance for hydrogenation of the aromatic compounds into naphthenic compounds in terms of activity that is at least as good as, or even better than, the processes known from the prior art.

The applicant has discovered that a nickel-based catalyst supported on alumina prepared using an organic additive chosen from organic compounds comprising at least one carboxylic acid function, or at least one alcohol function, or at least one ester function, or at least one amide function, when it is used in a process for the hydrogenation of aromatics, has improved catalytic performance, in terms of catalytic activity. This results in a better conversion of the feedstock under identical operating conditions.

SUBJECTS OF THE INVENTION

The present invention relates to a process for the hydrogenation of at least one aromatic or polyaromatic compound contained in a hydrocarbon feedstock having a final boiling point below or equal to 650° C., said process being carried out in the gas phase or in the liquid phase, at a temperature of between 30 and 350° C., at a pressure of between 0.1 and 20 MPa, at a hydrogen/(aromatic compounds to be hydrogenated) molar ratio between 0.1 and 10 and at an hourly space velocity HSV of between 0.05 and 50 $h^{-1}$, in the presence of a catalyst comprising an alumina support and an active phase comprising nickel, said active phase not comprising a metal from Group VIB, said catalyst being prepared by a process comprising at least:
  i) a step of bringing said support into contact with at least one solution containing at least one nickel precursor,
  ii) a step of bringing said support into contact with at least one solution containing at least one organic compound comprising at least one carboxylic acid function, or at least one alcohol function, or at least one ester function, or at least one amide function;
  iii) a step of drying said impregnated support at a temperature below 250° C.;
steps i) and ii) being carried out separately, in any order, or at the same time.

According to one embodiment according to the invention, the process may further comprise at least one step iv) of calcining said dried catalyst obtained in step iii) at a temperature of between 250 and 1000° C.

In one embodiment according to the invention, steps i) and ii) of the process according to the invention are carried out at the same time.

In another embodiment according to the invention, step i) of the process according to the invention is carried out before step ii).

In yet another embodiment according to the invention, step ii) of the process according to the invention is carried out before step i).

Preferably, steps i) and/or ii) is (are) carried out by dry impregnation.

Advantageously, the content of the element nickel is between 8 and 65% by weight relative to the total weight of the catalyst.

In one embodiment according to the invention, said organic compound comprises at least one carboxylic acid function.

Preferably, said organic compound is chosen from monocarboxylic acids, dicarboxylic acids, tricarboxylic acids or tetracarboxylic acids.

In one embodiment according to the invention, said organic compound comprises at least one alcohol function.

Preferably, said organic compound is chosen from:
organic compounds comprising a single alcohol function;
organic compounds comprising two alcohol functions;
organic compounds chosen from diethylene glycol, triethylene glycol, tetraethylene glycol or a polyethylene glycol corresponding to the formula $H(OC_2H_4)_nOH$ with n greater than 4 and having an average molar mass of less than 20 000 g/mol;
monosaccharides of empirical formula $C_n(H_2O)_p$ with n between 3 and 12;
disaccharides, trisaccharides, or monosaccharide derivatives.

In one embodiment according to the invention, said organic compound comprises at least one ester function.

Preferably, said organic compound is chosen from:
carboxylic acid linear or cyclic or unsaturated cyclic esters;
organic compounds comprising at least two carboxylic acid ester functions;
organic compounds comprising at least one carboxylic acid ester function and at least one second functional group chosen from alcohols, ethers, ketones or aldehydes;
carbonic acid cyclic or linear esters;
carbonic acid linear diesters.

In one embodiment according to the invention, said organic compound comprises at least one amide function.

Preferably, said organic compound is chosen from:
acyclic amides comprising one or two amide functions;
cyclic amides or lactams;
organic compounds comprising at least one amide function and a carboxylic acid function or an alcohol function;
organic compounds comprising at least one amide function and an additional nitrogen heteroatom.

In one embodiment according to the invention, an aromatic hydrogenation of benzene is carried out at a temperature of between 30 and 250° C., at a pressure of between 0.1 and 10 MPa, at a hydrogen/(benzene) molar ratio between 0.1 and 10 and at an hourly space velocity HSV of between 0.05 and 50 $h^{-1}$.

DETAILED DESCRIPTION

Definitions

Hereinafter, groups of chemical elements are given according to the CAS classification (CRC Handbook of Chemistry and Physics, published by CRC Press, Editor in Chief D. R. Lide, $81^{st}$ edition, 2000-2001). For example, Group VIII according to the CAS classification corresponds to the metals of Columns 8, 9 and 10 according to the new IUPAC classification.

Textural and structural properties of the support and of the catalyst described below are determined by the characterization methods known to those skilled in the art. The total pore volume and the pore distribution are determined in the present invention by nitrogen porosimetry as described in the book "Adsorption by powders and porous solids. Principles, methodology and applications", written by F. Rouquérol, J. Rouquérol and K. Sing, Academic Press, 1999.

The specific surface area is understood to mean the BET specific surface area ($S_{BET}$ in $m^2/g$) determined by nitrogen adsorption in accordance with standard ASTM D 3663-78 developed from the Brunauer-Emmett-Teller method described in the journal "The Journal of American Society", 1938, 60 (309).

The size of the nickel nanoparticles is understood to mean the mean diameter of the nickel crystallites in oxide form. The mean diameter of the nickel crystallites in oxide form is determined by X-ray diffraction, from the width of the diffraction line located at the angle $2\theta=43°$ (i.e. along the crystallographic direction [200]) using the Scherrer equation. This method, used in X-ray diffraction on polycrystalline samples or powders, which links the full width at half maximum of the diffraction peaks to the size of the particles, is described in detail in the reference: Appl. Cryst. (1978), 11, 102-113, "Scherrer after sixty years: A survey and some new results in the determination of crystallite size", J. I. Langford and A. J. C. Wilson.

Description of the Process

One subject of the present invention is a process for the hydrogenation of at least one aromatic or polyaromatic compound contained in a hydrocarbon feedstock having a final boiling point below or equal to 650° C., generally between 20 and 650° C. and preferably between 20 and 450° C. Said hydrocarbon feedstock containing at least one aromatic or polyaromatic compound may be chosen from the following petroleum or petrochemical cuts: the reformate from catalytic reforming, kerosene, light gas oil, heavy gas oil, cracking distillates, such as FCC cycle oil, coker gas oil or hydrocracking distillates.

The content of aromatic or polyaromatic compounds contained in the hydrocarbon feedstock treated in the hydrogenation process according to the invention is generally between 0.1% and 80% by weight, preferably between 1% and 50% by weight and particularly preferably between 2% and 35% by weight, the percentage being based on the total weight of the hydrocarbon feedstock. The aromatic compounds present in said hydrocarbon feedstock are, for example, benzene or alkylaromatics, such as toluene, ethylbenzene, o-xylene, m-xylene or p-xylene, or else aromatics having several aromatic rings (polyaromatics), such as naphthalene.

The sulfur or chlorine content of the feedstock is generally less than 5000 ppm by weight of sulfur or chlorine, preferably less than 100 ppm by weight and particularly preferably less than 10 ppm by weight.

The technological implementation of the process for the hydrogenation of aromatic or polyaromatic compounds is, for example, carried out by upflow or downflow injection of the hydrocarbon feedstock and of the hydrogen into at least one fixed bed reactor. Said reactor may be of isothermal type or of adiabatic type. An adiabatic reactor is preferred. The hydrocarbon feedstock may advantageously be diluted by one or more reinjection(s) of the effluent, resulting from said reactor where the reaction for the hydrogenation of the aromatics takes place, at various points of the reactor, located between the inlet and the outlet of the reactor, in order to limit the temperature gradient in the reactor. The technological implementation of the process for the hydrogenation of the aromatics according to the invention may also advantageously be carried out by the implantation of said supported catalyst in a reactive distillation column or in reactors-exchangers or in a slurry-type reactor. The stream of hydrogen may be introduced at the same time as the feedstock to be hydrogenated and/or at one or more different points of the reactor.

The hydrogenation of the aromatic or polyaromatic compounds may be carried out in the gas phase or in the liquid phase, preferably in the liquid phase. Generally, the hydrogenation of the aromatic or polyaromatic compounds is carried out at a temperature of between 30 and 350° C., preferably between 50 and 325° C., at a pressure of between 0.1 and 20 MPa, preferably between 0.5 and 10 MPa, at a hydrogen/(aromatic compounds to be hydrogenated) molar ratio between 0.1 and 10 and at an hourly space velocity HSV of between 0.05 and 50 $h^{-1}$, preferably between 0.1 and 10 $h^{-1}$, of a hydrocarbon feedstock containing aromatic or polyaromatic compounds and having a final boiling point below or equal to 650° C., generally between 20 and 650° C. and preferably between 20 and 450° C.

The hydrogen flow rate is adjusted in order to have available a sufficient amount thereof to theoretically hydrogenate all of the aromatic compounds and to maintain an excess of hydrogen at the reactor outlet.

The conversion of the aromatic or polyaromatic compounds is generally greater than 20 mol %, preferably greater than 40 mol %, more preferably greater than 80 mol % and particularly preferably greater than 90 mol % of the aromatic or polyaromatic compounds contained in the hydrocarbon feedstock. The conversion is calculated by dividing the difference between the total moles of the aromatic or polyaromatic compounds in the hydrocarbon feedstock and in the product by the total moles of the aromatic or polyaromatic compounds in the hydrocarbon feedstock.

According to a specific alternative form of the process according to the invention, a process for the hydrogenation of the benzene of a hydrocarbon feedstock, such as the reformate resulting from a catalytic reforming unit, is carried out. The benzene content in said hydrocarbon feedstock is generally between 0.1% and 40% by weight, preferably between 0.5% and 35% by weight and particularly preferably between 2% and 30% by weight, the percentage by weight being based on the total weight of the hydrocarbon feedstock.

The sulfur or chlorine content of the feedstock is generally less than 10 ppm by weight of sulfur or chlorine respectively and preferably less than 2 ppm by weight.

The hydrogenation of the benzene contained in hydrocarbon feedstock may be carried out in the gas phase or in the liquid phase, preferably in the liquid phase. When it is carried out in the liquid phase, a solvent may be present, such as cyclohexane, heptane or octane. Generally, the hydrogenation of the benzene is carried out at a temperature of between 30 and 250° C., preferably between 50 and 200° C. and more preferably between 80 and 180° C., at a pressure of between 0.1 and 10 MPa, preferably between 0.5 and 4 MPa, at a hydrogen/(benzene) molar ratio between 0.1 and 10 and at an hourly space velocity HSV of between 0.05 and 50 $h^{-1}$, preferably between 0.5 and 10 $h^{-1}$.

The conversion of the benzene is generally greater than 50 mol %, preferably greater than 80 mol %, more preferably greater than 90 mol % and particularly preferably greater than 98 mol %.

The process for the hydrogenation of the aromatic or polyaromatic compounds according to the invention is carried out in the presence of a catalyst comprising an alumina support and an active phase comprising nickel, said active phase not comprising a metal from Group VIB, said catalyst being prepared by a process comprising at least:

i) a step of bringing said support into contact with at least one solution containing at least one nickel precursor, ii) a step of bringing said support into contact with at least one solution containing at least one organic compound chosen from the organic compounds comprising at least one carboxylic acid function, or at least one alcohol function, or at least one ester function, or at least one amide function;

iii) a step of drying said impregnated support at a temperature below 250° C., so as to obtain a dried catalyst;

steps i) and ii) being carried out separately, in any order, or at the same time.

Description of the Catalyst

The catalyst used for the implementation of the process for the hydrogenation of the aromatic or polyaromatic compounds according to the invention comprises an active phase deposited on a support comprising alumina, said active phase comprising nickel. Said active phase is free of metals belonging to Group VIB (Cr, Mo, W) of the Periodic Table of the Elements. More particularly, the active phase does not comprise molybdenum or tungsten. More preferentially still, the active phase consists of nickel. According to the invention, the content of element nickel in the catalyst is between 8% and 65% by weight of the mass of catalyst, preferably between 12 and 55% by weight, more preferentially between 15 and 40% by weight, and more preferentially still between 18% and 35% by weight. The Ni content is measured by X-ray fluorescence.

The nickel is in the form of nanoparticles deposited on said support. The size of the nickel nanoparticles in the catalyst, measured in their oxide form, is less than or equal to 18 nm, preferably less than or equal to 15 nm, more preferentially between 0.5 and 12 nm, and even more preferentially between 1.5 and 10 nm.

The active phase of said catalyst also advantageously comprises at least one additional metal chosen from the metals from Group VIII, the metals from Group IB and/or tin. Preferably, the additional metal from Group VIII is chosen from palladium, platinum, ruthenium, rhodium and iridium. Preferably, the additional metal from Group IB is chosen from copper, gold and silver. Said additional metal(s) is (are) preferentially present with a content representing from 0.01% to 20% by weight of the mass of the catalyst, preferably from 0.05% to 10% by weight of the mass of the catalyst and more preferably still from 0.05% to 5% by weight of the mass of said catalyst. The tin is preferentially present at a content representing from 0.02% to 15% by weight of the mass of the catalyst, so that the Sn/Ni molar ratio is between 0.01 and 0.2, preferably between 0.025 to 0.055, and more preferably still between 0.03 to 0.05.

The catalyst used within the context of the process for the hydrogenation of the aromatic or polyaromatic compounds according to the invention is generally present in all forms known to those skilled in the art, for example in the form of beads, extrudates, tablets, pellets, hollow cylinders or irregular and nonspherical agglomerates, the specific shape of which may result from a crushing step.

In one particular embodiment according to the invention, the catalyst consists of extrudates having a diameter generally of between 0.5 and 10 mm, preferably between 0.8 and 3.2 mm and very preferably between 1.0 and 2.5 mm. This catalyst may advantageously be presented in the form of cylindrical, multilobal, trilobal or quadrilobal extrudates. Preferably, its shape will be trilobal or quadrilobal. The shape of the lobes could be adjusted according to all the methods known from the prior art.

In another particular embodiment according to the invention, the catalyst is in the form of beads having a diameter of between 0.5 and 8 mm, preferably between 0.7 and 5 mm and more preferentially still between 1 and 3 mm.

The support on which said active phase is deposited comprises alumina ($Al_2O_3$). Preferably, the alumina present in said support is a transition alumina, such as a γ-, δ-, θ-, χ-, ρ-, η- or κ-alumina, or α-alumina alone or as a mixture. More preferably, the alumina is a γ, δ or θ transition alumina, alone or as a mixture.

The support may comprise another oxide different from alumina, such as silica ($SiO_2$), titanium dioxide ($TiO_2$), ceria ($CeO_2$) and zirconia ($ZrO_2$). The support may be a silica-alumina. Very preferably, said support consists solely of alumina.

The pore volume of the support is generally between 0.1 $cm^3/g$ and 1.5 $cm^3/g$, preferably between 0.5 $cm^3/g$ and 1.0 $cm^3/g$. The specific surface area of the support is generally greater than or equal to 30 $m^2/g$, preferably greater than or equal to 50 $m^2/g$, more preferentially between 60 $m^2/g$ and 500 $m^2/g$, and more preferentially still between 100 $m^2/g$ and 400 $m^2/g$.

Description of the Catalyst Preparation Process

Generally, the catalyst used within the context of the process for the hydrogenation of the aromatic or polyaromatic compounds according to the invention is prepared by a process comprising at least the following steps:
i) a step of bringing said support into contact with at least one solution containing at least one nickel precursor;
ii) a step of bringing said support into contact with at least one solution containing at least one organic compound comprising at least one carboxylic acid function, or at least one alcohol function, or at least one ester function, or at least one amide function;
iii) a step of drying said impregnated support at a temperature below 250° C., so as to obtain a dried catalyst;

steps i) and ii) being carried out separately, in any order, or at the same time.

Step i) Bringing the Nickel Precursor into Contact with the Support

The deposition of the nickel on said support, in accordance with the implementation of said step i), may be carried out by any method well known to those skilled in the art. In particular, said step i) may be carried out by dry impregnation, by excess impregnation, or else by deposition-precipitation according to methods well known to those skilled in the art.

Said step i) is preferably carried out by impregnation of the support consisting, for example, in bringing said support into contact with at least one solution, which is aqueous or organic (for example methanol or ethanol or phenol or acetone or toluene or dimethyl sulfoxide (DMSO)) or else consists of a mixture of water and of at least one organic solvent, containing at least one nickel precursor at least partially in the dissolved state, or else in bringing said support into contact with at least one colloidal solution of at least one precursor of the nickel, in the oxidized form (nanoparticles of oxides, of oxy(hydroxide) or of hydroxide of the nickel) or in the reduced form (metal nanoparticles of the nickel in the reduced state). Preferably, the solution is aqueous. The pH of this solution could be modified by the optional addition of an acid or of a base. According to another preferred alternative form, the aqueous solution may contain ammonia or ammonium $NH_4^+$ ions.

Preferably, said step i) is carried out by dry impregnation, which consists in bringing the catalyst support into contact with a solution containing at least one nickel precursor, of which the volume of the solution is between 0.25 and 1.5 times the pore volume of the support to be impregnated.

When the nickel precursor is introduced in aqueous solution, use is advantageously made of a nickel precursor in the nitrate, carbonate, chloride, sulfate, hydroxide, hydroxycarbonate, formate, acetate or oxalate form, in the form of complexes formed with acetylacetonates, or else in the form of tetrammine or hexammine complexes, or in the form of any other inorganic derivative which is soluble in aqueous solution, which is brought into contact with said support. Use is advantageously made, as nickel precursor, of nickel nitrate, nickel carbonate, nickel chloride, nickel hydroxide or nickel hydroxycarbonate. Very preferably, the nickel precursor is nickel nitrate, nickel carbonate or nickel hydroxide.

The amounts of the nickel precursor(s) introduced into the solution are chosen so that the total content of element nickel is between 8% and 65% by weight of the mass of catalyst, preferably between 12% and 55% by weight, more preferentially between 15% and 40% by weight, and more preferentially still between 18% and 35% by weight.

In the embodiment in which step i) is carried out by dry impregnation or excess impregnation, preferably dry impregnation, the impregnation of the nickel with the support may advantageously be carried out via at least two impregnation cycles, using identical or different nickel precursors in each cycle. In this case, each impregnation is advantageously followed by drying and optionally a heat treatment.

Any other additional element may be introduced either at the time of the step of bringing the nickel into contact with the support or in another step different from bringing said additional element into contact with the support. When it is desired to introduce an additional metal chosen from the metals from Group VIII, the metals from Group IB and/or tin, use is advantageously made, as precursor, of a salt chosen from the nitrate, sulfate or chloride, or any other conventional precursor. When any other additional element is introduced in a step different from bringing said additional element into contact with the support, said step may be followed by drying and optionally a heat treatment.

Step ii) Bringing the Organic Compound into Contact with the Support

Said support may be bought into contact with at least one solution containing at least one organic compound comprising at least one carboxylic acid function, or at least one alcohol function, or at least one ester function, or at least one amide function, in accordance with the implementation of said step ii), by any method well known to those skilled in the art. In particular, said step ii) may be carried out by dry impregnation or by excess impregnation according to methods well known to those skilled in the art. Preferably, said step ii) is carried out by dry impregnation, which consists in bringing the catalyst support into contact with a volume of said solution of between 0.25 and 1.5 times the pore volume of the support to be impregnated.

Said solution containing at least one organic compound comprising at least one carboxylic acid function, or at least one alcohol function, or at least one ester function, or at least one amide function, may be aqueous or organic (for example methanol or ethanol or phenol or acetone or toluene or dimethyl sulfoxide (DMSO)) or else consist of a mixture of water and of at least one organic solvent. Said organic compound is, beforehand, at least partially dissolved in said solution at the desired concentration. Preferably, said solution is aqueous or contains ethanol. More preferably still, said solution is aqueous. The pH of said solution could be modified by the optional addition of an acid or of a base. In another possible embodiment, the solvent may be absent from the impregnation solution.

In the embodiment in which step ii) is carried out by dry impregnation or excess impregnation, preferably dry impregnation, the impregnation of the support with at least one solution containing at least said organic compound may advantageously be carried out via at least two impregnation cycles, using identical or different organic compounds in each cycle. In this case, each impregnation is advantageously followed by drying and optionally a heat treatment.

A) Organic Compound Comprising at Least One Carboxylic Acid Function

In one embodiment according to the invention, the organic compound comprises at least one carboxylic acid function. The molar ratio of said organic compound comprising at least one carboxylic acid function introduced during step ii) with respect to the element nickel introduced in step i) is between 0.01 and 5.0 mol/mol, preferably between 0.05 and 2.0 mol/mol, more preferentially between 0.1 and 1.5 mol/mol and more preferentially still between 0.3 and 1.2 mol/mol.

Said organic compound comprising at least one carboxylic acid function may be a saturated or unsaturated aliphatic organic compound or an aromatic organic compound. Preferably, the saturated or unsaturated aliphatic organic compound comprises between 1 and 9 carbon atoms, preferably between 2 and 7 carbon atoms. Preferably, the aromatic organic compound comprises between 7 and 10 carbon atoms, preferably between 7 and 9 carbon atoms.

Said saturated or unsaturated aliphatic organic compound or said aromatic organic compound comprising at least one carboxylic acid function may be chosen from monocarboxylic acids, dicarboxylic acids, tricarboxylic acids or tetracarboxylic acids.

In a specific embodiment of the invention, said organic compound is a saturated aliphatic monocarboxylic acid, the aliphatic chain being linear or branched or cyclic. When the organic compound is a saturated linear monocarboxylic acid, it is preferably chosen from formic acid, acetic acid, propionic acid, butanoic acid, valeric acid, hexanoic acid, heptanoic acid, octanoic acid or nonanoic acid. When the organic compound is a saturated branched monocarboxylic acid, it is preferably chosen from isobutyric acid, pivalic acid, 4-methyloctanoic acid, 3-methylvaleric acid, 4-methylvaleric acid, 2-methylvaleric acid, isovaleric acid, 2-ethylhexanoic acid, 2-methylbutyric acid, 2-ethylbutyric acid, 2-propylvalerianic acid or valproic acid, in any one of the isomeric forms thereof. When the organic compound is a saturated cyclic monocarboxylic acid, it is preferably chosen from cyclopentanecarboxylic acid or cyclohexanecarboxylic acid.

In a specific embodiment of the invention, said organic compound is an unsaturated aliphatic monocarboxylic acid, the aliphatic chain being linear or branched or cyclic, preferably chosen from methacrylic acid, acrylic acid, vinylacetic acid, crotonic acid, isocrotonic acid, penten-2-oic acid, penten-3-oic acid, penten-4-oic acid, tiglic acid, angelic acid, sorbic acid or acetylenecarboxylic acid, in any one of the isomeric forms thereof.

In a specific embodiment of the invention, said organic compound is an aromatic monocarboxylic acid preferably chosen from benzoic acid, methylbenzoic acid, dimethylbenzoic acid, trimethylbenzoic acid, ethylbenzoic acid, o-tolylacetic acid, phenylacetic acid, 2-phenylpropionic acid, 3-phenylpropionic acid, 4-vinylbenzoic acid, phenylacetylenecarboxylic acid or cinnamic acid, in any one of the isomeric forms thereof.

In a specific embodiment of the invention, said organic compound is a saturated or unsaturated aliphatic dicarboxylic acid, the aliphatic chain being linear or branched or cyclic.

When the organic compound is a saturated linear dicarboxylic acid, it is preferably chosen from ethanedioic acid (oxalic acid), propanedioic acid (malonic acid), butanedioic acid (succinic acid), pentanedioic acid (glutaric acid), hexanedioic acid (adipic acid), heptanedioic acid (pimelic acid), octanedioic acid (suberic acid) or nonanedioic acid (azelaic acid). When the organic compound is a saturated branched dicarboxylic acid, it is preferably chosen from 2-methylglutaric acid, 3-methylglutaric acid, 3,3-dimethylglutaric acid, 2,2-dimethylglutaric acid or butane-1,2-dicarboxylic acid, in any one of the isomeric forms thereof.

When the organic compound is a saturated cyclic dicarboxylic acid, it is preferably chosen from cyclohexanedicarboxylic acid or pinic acid, in any one of the isomeric forms thereof.

Preferably, said organic compound is chosen from ethanedioic acid (oxalic acid), propanedioic acid (malonic acid), butanedioic acid (succinic acid), pentanedioic acid (glutaric acid), 1,2-cyclohexanedicarboxylic acid or 1,3-cyclohexanedicarboxylic acid, in any one of the isomeric forms thereof. More preferably still, said organic compound is chosen from ethanedioic acid (oxalic acid), propanedioic acid (malonic acid), butanedioic acid (succinic acid) or pentanedioic acid (glutaric acid).

When the organic compound is an unsaturated, linear or branched or cyclic, dicarboxylic acid, it is preferably chosen from (Z)-butenedioic acid (maleic acid), (E)-butenedioic acid (fumaric acid), pent-2-enedioic acid (glutaconic acid), (2E,4E)-hexa-2,4-dienedioic acid (muconic acid), mesaconic acid, citraconic acid, acetylenedicarboxylic acid, 2-methylenesuccinic acid (itaconic acid) or hexa-2,4-dienedioic acid, in any one of the isomeric forms thereof.

Preferably, said organic compound is chosen from (Z)-butenedioic acid (maleic acid), (E)-butenedioic acid (fumaric acid), pent-2-enedioic acid (glutaconic acid), mesaconic acid, citraconic acid or 2-methylenesuccinic acid (itaconic acid), in any one of the isomeric forms thereof. More preferably still, said organic compound is chosen from (Z)-butenedioic acid (maleic acid), (E)-butenedioic acid (fumaric acid) or pent-2-enedioic acid (glutaconic acid).

In a specific embodiment of the invention, said organic compound is an aromatic dicarboxylic acid preferably chosen from benzene-1,2-dicarboxylic acid (phthalic acid), benzene-1,3-dicarboxylic acid (isophthalic acid), benzene-1,4-dicarboxylic acid (terephthalic acid) or phenylsuccinic acid, in any one of the isomeric forms thereof. Preferably, said organic compound is benzene-1,2-dicarboxylic acid (phthalic acid).

In a specific embodiment of the invention, said organic compound is a saturated or unsaturated aliphatic or aromatic tricarboxylic acid preferably chosen from 1,2,3-propanetricarboxylic acid (tricarballylic acid), 1,2,4-butanetricarboxylic acid, 1,2,3-propenetricarboxylic acid (aconitic acid), 1,3,5-benzenetricarboxylic acid (trimesic acid) or 1,2,4-benzenetricarboxylic acid, in any one of the isomeric forms thereof. Preferably, said organic compound is chosen from 1,2,3-propanetricarboxylic acid (tricarballylic acid), 1,2,4-butanetricarboxylic acid, 1,2,3-propenetricarboxylic acid (aconitic acid) or 1,2,4-benzenetricarboxylic acid, in any one of the isomeric forms thereof.

In a specific embodiment of the invention, said organic compound is a saturated or unsaturated aliphatic or aromatic tetracarboxylic acid preferably chosen from methanetetracarboxylic acid, 1,2,3,4-butanetetracarboxylic acid, ethylenetetracarboxylic acid or 1,2,4,5-benzenetetracarboxylic acid, in any one of the isomeric forms thereof. Preferably, said organic compound is chosen from 1,2,3,4-butanetetracarboxylic acid or 1,2,4,5-benzenetetracarboxylic acid, in any one of the isomeric forms thereof.

In another embodiment according to the invention, said organic compound may comprise at least one second functional group chosen from ethers, hydroxyls, ketones or esters. Advantageously, said organic compound comprises at least one carboxylic acid function and at least one hydroxyl function, or at least one carboxylic acid function and at least one ether function, or at least one carboxylic acid function and at least one ketone function. Advantageously, said organic compound may comprise at least three different functional groups chosen from at least one carboxylic acid function, at least one hydroxyl function and at least one functional group other than the carboxylic acid and hydroxyl functions, such as an ether function or a ketone function.

Mention may be made, among organic compounds comprising at least one carboxylic acid function and at least one hydroxyl function, of hydroxy acids of monocarboxylic acids, hydroxy acids of dicarboxylic acids or of polycarboxylic acids, dihydroxy acids of monocarboxylic acids or of polycarboxylic acids, trihydroxy acids of monocarboxylic acids or of polycarboxylic acids, and more generally polyhydroxy acids of monocarboxylic acids or of polycarboxylic acids, it being possible for the carbon chain of said acids to be saturated (linear, branched or cyclic) aliphatic or unsaturated (linear, branched or cyclic) aliphatic or to contain at least one aromatic ring. Preferably, said organic compound is chosen from hydroxy acids or dihydroxy acids of monocarboxylic acids or of dicarboxylic acids or of tricarboxylic acids.

When the organic compound is a hydroxy acid of a monocarboxylic acid, it is preferably chosen from hydroxyacetic acid (glycolic acid), 2-hydroxypropanoic acid (lactic acid), 2-hydroxyisobutyric acid or the other α-hydroxy acids, 3-hydroxypropanoic acid, 3-hydroxybutyric acid, 3-hydroxypentanoic acid, 3-hydroxyisobutyric acid, 3-hydroxy-3-methylbutanoic acid or the other β-hydroxy acids, 4-hydroxybutyric acid or the other γ-hydroxy acids, mandelic acid, 3-phenyllactic acid, tropic acid, hydroxybenzoic acid, salicylic acid, (2-hydroxyphenyl)acetic acid, (3-hydroxyphenyl)acetic acid, (4-hydroxyphenyl)acetic acid or coumaric acid, in any one of the isomeric forms thereof. Preferably, said organic compound is chosen from hydroxyacetic acid (glycolic acid), 2-hydroxypropanoic acid (lactic acid), 3-hydroxypropanoic acid, 3-hydroxybutyric acid, 3-hydroxyisobutyric acid, mandelic acid, 3-phenyllactic acid, tropic acid or salicylic acid, in any one of the isomeric forms thereof. More preferably still, said organic compound is chosen from hydroxyacetic acid (glycolic acid), 2-hydroxypropanoic acid (lactic acid), 3-hydroxypropanoic acid, 3-hydroxybutyric acid or 3-hydroxyisobutyric acid.

When the organic compound is hydroxy acid of a polycarboxylic acid, it is preferably chosen from 2-hydroxypropanedioic acid (tartronic acid), 2-hydroxybutanedioic acid (malic acid), acetolactic acid or the other α-hydroxy acids or β-hydroxy acids or γ-hydroxy acids of dicarboxylic acids, 5-hydroxyisophthalic acid, 2-hydroxypropane-1,2,3-tricarboxylic acid (citric acid), isocitric acid, homocitric acid, homoisocitric acid or the other α-hydroxy acids or (3-hydroxy acids or γ-hydroxy acids of tricarboxylic acids, in any one of the isomeric forms thereof. Preferably, said organic compound is chosen from 2-hydroxypropanedioic acid (tartronic acid), 2-hydroxybutanedioic acid (malic acid), acetolactic acid, 2-hydroxypropane-1,2,3-tricarboxylic acid (citric acid), isocitric acid, homocitric acid or homoisocitric acid, in any one of the isomeric forms thereof. More preferably still, said organic compound is chosen from 2-hydroxypropanedioic acid (tartronic acid), 2-hydroxybutanedioic acid (malic acid), acetolactic acid or 2-hydroxypropane-1,2,3-tricarboxylic acid (citric acid).

When the organic compound is a dihydroxy acid of a monocarboxylic acid, it is preferably chosen from glyceric acid, 2,3-dihydroxy-3-methylpentanoic acid, pantoic acid or the other α,α-dihydroxy acids or α,β-dihydroxy acids or α,γ-dihydroxy acids, 3,5-dihydroxy-3-methylpentanoic acid (mevalonic acid) or the other β,β-dihydroxy acids or β,γ-dihydroxy acids or γ,γ-dihydroxy acids, bis(hydroxymethyl)-2,2-propionic acid, 2,3-dihydroxybenzoic acid, α-resorcylic acid, β-resorcylic acid, γ-resorcylic acid, gentisic acid, protocatechuic acid, orsellinic acid, homogentisic acid or caffeic acid, in any one of their isomeric forms. Preferably, said organic compound is chosen from glyceric acid, 2,3-dihydroxy-3-methylpentanoic acid, pantoic acid, 2,3-dihydroxybenzoic acid, β-resorcylic acid, γ-resorcylic acid, gentisic acid or orsellinic acid, in any one of the isomeric forms thereof. More preferably still, said organic compound is chosen from glyceric acid, 2,3-dihydroxy-3-methylpentanoic acid or pantoic acid.

When the organic compound is a dihydroxy acid of a polycarboxylic acid, it is preferably chosen from dihydroxymalonic acid, 2,3-dihydroxybutanedioic acid (tartaric acid) or the other α,α-dihydroxy acids or α,β-dihydroxy acids or α,γ-dihydroxy acids or β,β-dihydroxy acids or β,γ-dihydroxy acids or γ,γ-dihydroxy acids of dicarboxylic acids, or hydroxycitric acid, in any one of the isomeric forms thereof. Preferably, said organic compound is chosen from dihydroxymalonic acid, 2,3-dihydroxybutanedioic acid (tartaric acid) or hydroxycitric acid, in any one of the isomeric forms thereof. More preferably still, said organic compound is chosen from dihydroxymalonic acid or 2,3-dihydroxybutanedioic acid (tartaric acid).

When the organic compound is a polyhydroxy acid of a monocarboxylic acid or of a polycarboxylic acid, it is preferably chosen from shikimic acid, trihydroxybenzoic acid, gallic acid, phloroglucinic acid, pyrogallolcarboxylic acid, quinic acid, gluconic acid, mucic acid or saccharic acid, in any one of the isomeric forms thereof. Preferably, said organic compound is chosen from trihydroxybenzoic acid, quinic acid, gluconic acid, mucic acid or saccharic acid, in any one of the isomeric forms thereof. More preferably still, said organic compound is chosen from quinic acid, gluconic acid, mucic acid or saccharic acid.

Mention may be made, among the organic compounds comprising at least one carboxylic acid function and at least one ether function, of 2-methoxyacetic acid, 2,2'-oxydiacetic acid (diglycolic acid), 4-methoxybenzoic acid, 4-isopropoxybenzoic acid, 3-methoxyphenylacetic acid, 3-methoxycinnamic acid, 4-methoxycinnamic acid, 3,4-dimethoxycinnamic acid, veratric acid, tetrahydrofuran-2-carboxylic acid, furan-3-carboxylic acid or 2,5-dihydrofuran-3,4-dicarboxylic acid, according to any one of the isomeric forms thereof. Preferably, said organic compound is 2,2'-oxydiacetic acid (diglycolic acid).

Mention may be made, among the organic compounds comprising at least one carboxylic acid function and at least one ketone function, of glyoxylic acid, 2-oxopropanoic acid (pyruvic acid), 2-oxobutanoic acid, 3-oxopentanoic acid, 3-methyl-2-oxobutanoic acid, 4-methyl-2-oxopentanoic acid, phenylglyoxylic acid, phenylpyruvic acid, mesoxalic acid, 2-oxoglutaric acid, 2-oxohexanedioic acid, oxalosuccinic acid or the other α-keto acids of monocarboxylic acids or of polycarboxylic acids, acetylacetic acid, acetonedicarboxylic acid or the other β-keto acids of monocarboxylic acids or of polycarboxylic acids, 4-oxopentanoic acid (levulinic acid) or the other γ-keto acids of monocarboxylic acids or of polycarboxylic acids, 4-acetylbenzoic acid, dioxosuccinic acid, 4-maleylacetoacetic acid or the other polyketo acids of monocarboxylic acids or of polycarboxylic acids, in any one of the isomeric forms thereof. Preferably, said organic compound is chosen from glyoxylic acid, 2-oxopropanoic acid (pyruvic acid), 2-oxobutanoic acid, 3-methyl-2-oxobutanoic acid, phenylglyoxylic acid, phenylpyruvic acid, mesoxalic acid, 2-oxoglutaric acid, 2-oxohexanedioic acid, oxalosuccinic acid, acetylacetic acid, acetonedicarboxylic acid, 4-oxopentanoic acid (levulinic acid) or dioxosuccinic acid, according to any one of the isomeric forms thereof. More preferably still, said organic compound is chosen from glyoxylic acid, 2-oxopropanoic acid (pyruvic acid), 2-oxobutanoic acid, 3-methyl-2-oxobutanoic acid, mesoxalic acid, 2-oxoglutaric acid, acetylacetic acid, acetonedicarboxylic acid, 4-oxopentanoic acid (levulinic acid) or dioxosuccinic acid.

Mention may be made, among the organic compounds comprising at least one carboxylic acid function and at least one ester function, of acetylsalicylic acid.

Mention may be made, among the organic compounds comprising at least one carboxylic acid function, at least one hydroxyl function and at least one ether function, of 4-hydroxy-3-methoxybenzoic acid (vanillic acid), syringic acid, glucuronic acid, galacturonic acid, ferulic acid or sinapinic acid, according to any one of the isomeric forms thereof. Preferably, said organic compound is chosen from 4-hydroxy-3-methoxybenzoic acid (vanillic acid), glucuronic acid or galacturonic acid, according to any one of the isomeric forms thereof.

Mention may be made, among the organic compounds comprising at least one carboxylic acid function, at least one hydroxyl function and at least one ketone function, of hydroxypyruvic acid, acetolactic acid, iduronic acid, ulosonic acid, meconic acid or 4-hydroxyphenylpyruvic acid, according to any one of the isomeric forms thereof. Preferably, said organic compound is chosen from hydroxypyruvic acid, acetolactic acid, iduronic acid or meconic acid, according to any one of the isomeric forms thereof.

Among all the preceding embodiments, said organic compound comprising at least one carboxylic acid function is preferably chosen from ethanedioic acid (oxalic acid), propanedioic acid (malonic acid), butanedioic acid (succinic acid), pentanedioic acid (glutaric acid), 1,2-cyclohexanedicarboxylic acid, 1,3-cyclohexanedicarboxylic acid, (Z)-butenedioic acid (maleic acid), (E)-butenedioic acid (fumaric acid), pent-2-enedioic acid (glutaconic acid), mesaconic acid, citraconic acid, 2-methylenesuccinic acid (itaconic acid), benzene-1,2-dicarboxylic acid (phthalic acid), 1,2,3-propanetricarboxylic acid (tricarballylic acid), 1,2,4-butanetricarboxylic acid, 1,2,3-propenetricarboxylic acid (aconitic acid), 1,2,4-benzenetricarboxylic acid, 1,2,3,4-butanetetracarboxylic acid, 1,2,4,5-benzenetetracarboxylic acid, hydroxyacetic acid (glycolic acid), 2-hydroxypropanoic acid (lactic acid), 3-hydroxypropanoic acid, 3-hydroxybutyric acid, 3-hydroxyisobutyric acid, mandelic acid, 3-phenyllactic acid, tropic acid, salicylic acid, glyceric acid, 2,3-dihydroxy-3-methylpentanoic acid, pantoic acid, 2,3-dihydroxybenzoic acid, (3-resorcylic acid, γ-resorcylic acid, gentisic acid, orsellinic acid, dihydroxymalonic acid, 2,3-dihydroxybutanedioic acid (tartaric acid), hydroxycitric acid, trihydroxybenzoic acid, quinic acid, gluconic acid, mucic acid, saccharic acid, 2,2'-oxydiacetic acid (diglycolic acid), glyoxylic acid, 2-oxopropanoic acid (pyruvic acid), 2-oxobutanoic acid, 3-methyl-2-oxobutanoic acid, phenylglyoxylic acid, phenylpyruvic acid, mesoxalic acid, 2-oxoglutaric acid, 2-oxohexanedioic acid, oxalosuccinic acid, acetylacetic acid, acetonedicarboxylic acid, 4-oxopentanoic acid (levulinic acid), dioxosuccinic acid, 4-hydroxy-3-methoxybenzoic acid (vanillic acid), glucuronic acid, galacturonic acid, hydroxypyruvic acid, acetolactic acid, iduronic acid or meconic acid, according to any one of the isomeric forms thereof.

Among all the preceding embodiments, said organic compound comprising at least one carboxylic acid function is more preferably chosen from ethanedioic acid (oxalic acid), propanedioic acid (malonic acid), butanedioic acid (succinic acid), pentanedioic acid (glutaric acid), (Z)-butenedioic acid (maleic acid), (E)-butenedioic acid (fumaric acid), pent-2-enedioic acid (glutaconic acid), hydroxyacetic acid (glycolic acid), 2-hydroxypropanoic acid (lactic acid), 3-hydroxypropanoic acid, 3-hydroxybutyric acid, 3-hydroxyisobutyric acid, 2-hydroxypropanedioic acid (tartronic acid), 2-hydroxybutanedioic acid (malic acid), acetolactic acid, 2-hydroxypropane-1,2,3-tricarboxylic acid (citric acid), glyceric acid, 2,3-dihydroxy-3-methylpentanoic acid, pantoic acid, dihydroxymalonic acid, 2,3-dihydroxybutanedioic acid (tartaric acid), quinic acid, gluconic acid, mucic acid, saccharic acid, glyoxylic acid, 2-oxopropanoic acid (pyruvic acid), 2-oxobutanoic acid, 3-methyl-2-oxobutanoic acid, mesoxalic acid, 2-oxoglutaric acid, acetylacetic acid, acetonedicarboxylic acid, 4-oxopentanoic acid (levulinic acid) or dioxosuccinic acid. More preferably still, the organic compound comprising at least one carboxylic acid function is chosen from ethanedioic acid (oxalic acid), propanedioic acid (malonic acid), pentanedioic acid (glutaric acid), hydroxyacetic acid (glycolic acid), 2-hydroxypropanoic acid (lactic acid), 2-hydroxypropanedioic acid (tartronic acid), 2-hydroxypropane-1,2,3-tricarboxylic acid (citric acid), 2,3-dihydroxybutanedioic acid (tartaric acid), 2-oxopropanoic acid (pyruvic acid) or 4-oxopentanoic acid (levulinic acid).

All the embodiments relating to the nature of said organic compound can be combined together so that step ii) may be carried out by bringing said support into contact with at least one solution containing at least one organic compound comprising at least one carboxylic acid function, in particular an organic compound comprising at least one carboxylic function as cited above.

According to one preferential embodiment, when said organic compound comprises at least one carboxylic acid function and at least one ketone function, step ii) is advantageously carried out before step i).

According to one preferential embodiment, when said organic compound comprises at least one carboxylic acid function and at least one hydroxyl function, step i) is advantageously carried out before step ii).

B) Organic Compound Comprising at Least One Alcohol Function

In another embodiment according to the invention, the organic compound comprises at least one alcohol function. The molar ratio of said organic compound comprising at least one alcohol function introduced during step ii) with respect to the element nickel introduced in step i) is between 0.01 and 5.0 mol/mol, preferably between 0.05 and 1.5 mol/mol, more preferentially between 0.08 and 0.9 mol/mol.

Preferably, said organic compound comprises between 2 and 20 carbon atoms, preferably between 2 and 12 carbon atoms and more preferably still between 2 and 8 carbon atoms.

In one embodiment according to the invention, the organic compound comprises a single alcohol function (monoalcohol). Preferably, the organic compound is chosen from methanol, ethanol, propanol, butanol, pentanol, hexanol, 2-propyn-1-ol, geraniol, menthol, phenol or cresol, in any one of the isomeric forms thereof. More preferably, said organic compound is chosen from methanol, ethanol or phenol.

In another embodiment according to the invention, the organic compound comprises at least two alcohol functions (diol or more generally polyol). Preferably, the organic compound is selected from ethylene glycol, propane-1,3-diol, butane-1,4-diol, pentane-1,5-diol, hexane-1,6-diol, heptane-1,7-diol, octane-1,8-diol, propane-1,2-diol, butane-1,2-diol, butane-2,3-diol, butane-1,3-diol, pentane-1,2-diol, pentane-1,3-diol, pentane-2,3-diol, pentane-2,4-diol, 2-ethylhexane-1,3-diol (etohexadiol), p-menthane-3,8-diol, 2-methylpentane-2,4-diol, but-2-yne-1,4-diol, 2,3,4-trihydroxypentane, 2,2-dihydroxyhexane, 2,2,4-trihydroxyhexane, glycerol, erythritol, threitol, arabitol, xylitol, ribitol, mannitol, sorbitol, dulcitol, allitol, glucitol, tolitol, fucitol, iditol, volemitol or inositol, in any one of the isomeric forms thereof. More preferably, said organic compound is chosen from ethylene glycol, propane-1,3-diol, butane-1,4-diol, pentane-1,5-diol, hexane-1,6-diol, glycerol, xylitol, mannitol or sorbitol, in any one of the isomeric forms thereof.

In another embodiment according to the invention, the organic compound is an aromatic organic compound comprising at least two alcohol functions. Preferably, the organic compound is selected from pyrocatechol, resorcinol, hydroquinone, pyrogallol, phloroglucinol, hydroxyquinol, tetrahydroxybenzene or benzenehexol, in any one of the isomeric forms thereof. More preferably, said organic compound is chosen from pyrocatechol, resorcinol or hydroquinone.

In another embodiment according to the invention, the organic compound can be selected from diethylene glycol, triethylene glycol, tetraethylene glycol or more generally polyethylene glycols corresponding to the formula $H(OC_2H_4)_nOH$ with n greater than 4 and having an average molar mass of less than 20 000 g/mol. More preferably, said organic compound is chosen from diethylene glycol, triethylene glycol or polyethylene glycols having an average molar mass of less than 600 g/mol.

In another embodiment according to the invention, the organic compound is a monosaccharide of empirical formula $C_n(H_2O)_n$ with n between 3 and 12, preferably between 3 and 10. Preferably, the organic compound is selected from glyceraldehyde, dihydroxyacetone, erythrose, threose, erythrulose, lyxose, arabinose, xylose, ribose, ribulose, xylulose, glucose, mannose, sorbose, galactose, fructose, allose, altrose, gulose, idose, talose, psicose, tagatose, sedoheptulose or mannoheptulose, in any one of the isomeric forms thereof. More preferably, said organic compound is chosen from glucose, mannose or fructose, in any one of the isomeric forms thereof.

In another embodiment according to the invention, the organic compound is a disaccharide or a trisaccharide, or a derivative of a monosaccharide, selected from sucrose, maltose, lactose, cellobiose, gentiobiose, inulobiose, isomaltose, isomaltulose, kojibiose, lactulose, laminaribiose, leucrose, maltulose, melibiose, nigerose, robinose, rutinose, sophorose, trehalose, trehalulose, turanose, erlose, fucosyllactose, gentianose, inulotriose, kestose, maltotriose, mannotriose, melezitose, neokestose, panose, raffinose, rhamninose, maltitol, lactitol, isomaltitol or isomaltulose, in any one of the isomeric forms thereof. More preferably, said organic compound is chosen from sucrose, maltose or lactose, in any one of the isomeric forms thereof.

In another embodiment according to the invention, the organic compound comprises at least one alcohol function, at least one ketone function and at least unsaturated heterocyclic preferably chosen from isomaltol, maltol, ethyl maltol, dehydroacetic acid, kojic acid or erythorbic acid, in any one of the isomeric forms thereof.

Among all the preceding embodiments, said organic compound comprising at least one alcohol function is preferably chosen from methanol, ethanol, propanol, butanol, pentanol, hexanol, 2-propyn-1-ol, geraniol, menthol, phenol, cresol, ethylene glycol, propane-1,3-diol, butane-1,4-diol, pentane-1,5-diol, hexane-1,6-diol, heptane-1,7-diol, octane-1,8-diol, propane-1,2-diol, butane-1,2-diol, butane-2,3-diol, butane-1,3-diol, pentane-1,2-diol, pentane-1,3-diol, pentane-2,3-diol, pentane-2,4-diol, 2-ethylhexane-1,3-diol, p-menthane-3,8-diol, 2-methylpentane-2,4-diol, but-2-yne-1,4-diol, 2,3,4-trihydroxypentane, 2,2-dihydroxyhexane, 2,2,4-trihydroxyhexane, glycerol, erythritol, threitol, arabitol, xylitol, ribitol, mannitol, sorbitol, dulcitol, allitol, glucitol, tolitol, fucitol, iditol, volemitol, inositol, pyrocatechol, resorcinol, hydroquinone, pyrogallol, phloroglucinol, hydroxyquinol, tetrahydroxybenzene, benzenehexol, diethylene glycol, triethylene glycol, tetraethylene glycol, polyethylene glycols corresponding to the formula $H(OC_2H_4)_nOH$ with n greater than 4 and having an average molar mass of less than 20 000 g/mol, glyceraldehyde, dihydroxyacetone, erythrose, threose, erythrulose, lyxose, arabinose, xylose, ribose, ribulose, xylulose, glucose, mannose, sorbose, galactose, fructose, allose, altrose, gulose, idose, talose, psicose, tagatose, sedoheptulose, mannoheptulose, sucrose, maltose, lactose, cellobiose, gentiobiose, inulobiose, isomaltose, isomaltulose, kojibiose, lactulose, laminaribiose, leucrose, maltulose, melibiose, nigerose, robinose, rutinose, sophorose, trehalose, trehalulose, turanose, erlose, fucosyllactose, gentianose, inulotriose, kestose, maltotriose, mannotriose, melezitose, neokestose, panose, raffinose, rhamninose, maltitol, lactitol, isomaltitol, isomaltulose, isomaltol, maltol, ethyl maltol, dehydroacetic acid, kojic acid or erythorbic acid, in any one of the isomeric forms thereof.

More preferably, said organic compound is chosen from methanol, ethanol, phenol, ethylene glycol, propane-1,3-diol, butane-1,4-diol, pentane-1,5-diol, hexane-1,6-diol, glycerol, xylitol, mannitol, sorbitol, pyrocatechol, resorcinol, hydroquinone, diethylene glycol, triethylene glycol, polyethylene glycols having an average molar mass of less than 600 g/mol, glucose, mannose, fructose, sucrose, maltose or lactose, in any one of the isomeric forms thereof.

All the embodiments relating to the nature of said organic compound can be combined together so that step ii) may be carried out by bringing said support into contact with at least one solution containing at least one organic compound comprising at least one alcohol function, in particular an organic compound comprising at least one alcohol function as cited above.

Preferably, when said organic compound comprises at least two alcohol functions (diol or more generally polyol), with the exception of compounds of diethylene glycol, triethylene glycol, tetraethylene glycol, or more generally polyethylene glycol type, step i) is carried out before step ii) or steps i) and ii) are carried out at the same time. More preferentially, step i) is carried out before step ii).

Preferably, when said organic compound is an aromatic organic compound comprising at least two alcohol functions, step i) is carried out before step ii), or steps i) and ii) are carried out at the same time.

Preferably, when said organic compound is a diethylene glycol, triethylene glycol, tetraethylene glycol, or more generally a polyethylene glycol corresponding to the formula $H(OC_2H_4)_nOH$ with n greater than 4 and having an average molar mass of less than 20 000 g/mol, step i) is carried out before step ii) or step ii) is carried out before step i). More preferentially, step ii) is carried out before step i).

Preferably, when said organic compound is a monosaccharide of empirical formula $C_n(H_2O)_p$ with n between 3 and 12, preferably between 3 and 10, or a disaccharide or a trisaccharide, or a derivative of a monosaccharide, step ii) is carried out before step i).

Preferably, when said organic compound comprises at least one alcohol function, at least one ketone function and at least one unsaturated heterocyclic, step i) is carried out before step ii) or step ii) is carried out before step i).

C) Organic Compound Comprising at Least One Ester Function

In another embodiment according to the invention, the organic compound comprises at least one ester function.

The molar ratio of said organic compound comprising at least one ester function introduced during step ii) with respect to the element nickel introduced in step i) is between 0.01 and 5.0 mol/mol, preferably between 0.05 and 2.0 mol/mol, more preferentially between 0.1 and 1.5 mol/mol and more preferentially still between 0.3 and 1.2 mol/mol.

Preferably, said organic compound comprises between 2 and 20 carbon atoms, preferably between 3 and 14 carbon atoms and more preferably still between 3 and 8 carbon atoms.

According to the invention, said organic compound comprises at least one ester function. It can be chosen from a linear or cyclic or unsaturated cyclic carboxylic acid ester, or a cyclic or linear carbonic acid ester, or also a linear carbonic acid diester.

In the case of a carboxylic acid cyclic ester, the compound can be a saturated cyclic ester. The term used is α-lactone, β-lactone, γ-lactone, δ-lactone or ε-lactone, depending on the number of carbon atoms in the heterocycle. Said compound can also be substituted by one or more alkyl group(s) or aryl group(s) or alkyl group(s) containing unsaturations. Preferably, said compound is a lactone containing between 4 and 12 carbon atoms, such as γ-butyrolactone, γ-valerolactone, δ-valerolactone, γ-caprolactone, δ-caprolactone, ε-caprolactone, γ-heptalactone, δ-heptalactone, γ-octalactone, δ-octalactone, δ-nonalactone, ε-nonalactone, decalactone, γ-decalactone, ε-decalactone, δ-dodecalactone or γ-dodecalactone, in any one of the isomeric forms thereof. More preferably still, said compound is a γ-lactone or a δ-lactone containing between 4 and 8 carbon atoms, γ-butyrolactone, γ-valerolactone, δ-valerolactone, γ-caprolactone, δ-caprolactone, γ-heptalactone, δ-heptalactone, γ-octalactone or δ-octalactone, in any one of the isomeric forms thereof. Preferably, the compound is γ-valerolactone.

In the case of a carboxylic acid unsaturated cyclic ester (containing unsaturations in the ring), the compound may be furan or pyrone or any one of the derivatives thereof, such as 6-pentyl-α-pyrone.

In the case of a carboxylic acid linear ester, the compound may be a compound comprising a single ester function corresponding to the empirical formula RCOOR', in which R and R' are linear, branched or cyclic alkyl groups, or alkyl groups containing unsaturations, or alkyl groups substituted by one or more aromatic rings, or aryl groups, each containing between 1 and 15 carbon atoms and which may be identical or different. The R group may also be the hydrogen atom H. Preferably, the R' group (of the alkoxy function COR') contains a number of carbon atoms which is less than or equal to that of the R group, more preferably still the number of carbon atoms of said R' group is between 1 and 6, more preferably still between 1 and 4. Said organic compound is preferably chosen from methyl methanoate, methyl acetate, methyl propanoate, methyl butanoate, methyl pentanoate, methyl hexanoate, methyl octanoate, methyl decanoate, methyl laurate, methyl dodecanoate, ethyl acetate, ethyl propanoate, ethyl butanoate, ethyl pentanoate or ethyl hexanoate. Preferably, the organic compound is methyl laurate.

In another embodiment according to the invention, the organic compound may be a compound comprising at least two carboxylic acid ester functions.

Advantageously, the carbon chain in which these carboxylic acid ester functions are inserted is a linear or branched or cyclic aliphatic carbon chain which is saturated or which can contain unsaturations, and contains between 2 and 15 carbon atoms, and each R' group (of each of the alkoxy functions COR') may be a linear, branched or cyclic alkyl group, or an alkyl group containing unsaturations, or an alkyl group substituted by one or more aromatic rings, or an aryl group, containing between 1 and 15 carbon atoms, preferably between 1 and 6 carbon atoms, more preferably still between 1 and 4 carbon atoms. The various R' groups can be identical or different. Preferably, said compound is chosen from dimethyl oxalate, dimethyl malonate, dimethyl succinate, dimethyl glutarate, dimethyl adipate, diethyl oxalate, diethyl malonate, diethyl succinate, diethyl glutarate, diethyl adipate, dimethyl methylsuccinate or dimethyl 3-methylglutarate, in any one of the isomeric forms thereof. More preferably, the compound is dimethyl succinate.

In another embodiment according to the invention, the organic compound may be a compound comprising at least one carboxylic acid ester function and at least one second functional group chosen from alcohols, ethers, ketones or aldehydes.

Advantageously, said organic compound comprises at least one carboxylic acid ester function and at least one alcohol function.

Preferably, the carbon chain in which the carboxylic acid ester function(s) is(are) inserted is a linear or branched or cyclic aliphatic carbon chain which is saturated or which can contain unsaturations, and contains between 2 and 15 carbon atoms, and each R' group (of each of the alkoxy functions COR') may be a linear, branched or cyclic alkyl group, or an alkyl group containing unsaturations, or an alkyl group substituted by one or more aromatic rings, or an aryl group, containing between 1 and 15 carbon atoms, preferably between 1 and 6 carbon atoms, more preferably still between 1 and 4 carbon atoms, it being possible for the various R' groups to be identical or different. This carbon chain contains at least one hydroxyl group, preferably between 1 and 6 hydroxyl groups.

Preferably, said compound is chosen from methyl glycolate, ethyl glycolate, butyl glycolate, benzyl glycolate, methyl lactate, ethyl lactate, butyl lactate, tert-butyl lactate, ethyl 3-hydroxybutyrate, ethyl mandelate, dimethyl malate, diethyl malate, diisopropyl malate, dimethyl tartrate, diethyl tartrate, diisopropyl tartrate, trimethyl citrate or triethyl citrate, in any one of the isomeric forms thereof. More preferably, said compound is dimethyl malate.

Advantageously, said organic compound comprises at least one carboxylic acid ester function and at least one ketone or aldehyde function. Preferably, the carbon chain in which the carboxylic acid ester function(s) is(are) inserted is a linear or branched or cyclic aliphatic carbon chain which is saturated or which can contain unsaturations, and contains between 2 and 15 carbon atoms, and each R' group (of each of the alkoxy functions COR') may be a linear, branched or cyclic alkyl group, or an alkyl group containing unsaturations, or an alkyl group substituted by one or more aromatic rings, or an aryl group, containing between 1 and 15 carbon atoms, preferably between 1 and 6 carbon atoms, more preferably still between 1 and 4 carbon atoms, it being possible for the various R' groups to be identical or different. This carbon chain contains at least one ketone or aldehyde function, preferably between 1 and 3 ketone or aldehyde function(s). Preferably, the organic compound is an aceto acid.

In the case of a carbonic acid cyclic ester, the compound can be ethylene carbonate, propylene carbonate or trimethylene carbonate. Preferably, the compound is propylene carbonate.

In the case of a carbonic acid linear ester, the compound can be dimethyl carbonate, diethyl carbonate or diphenyl carbonate.

In the case of a carbonic acid linear diester, the compound can be dimethyl dicarbonate, diethyl dicarbonate or di(tert-butyl) dicarbonate.

Advantageously, said organic compound may comprise at least three different functional groups chosen from at least one ester function, at least one carboxylic acid function and at least one functional group other than the ester and carboxylic acid functions, such as an ether function or a ketone function.

Among all the preceding embodiments, said organic compound comprising at least one ester function is preferably chosen from a γ-lactone or a δ-lactone containing between 4 and 8 carbon atoms, γ-butyrolactone, γ-valerolactone, δ-valerolactone, γ-caprolactone, δ-caprolactone, γ-heptalactone, δ-heptalactone, γ-octalactone, δ-octalactone, methyl methanoate, methyl acetate, methyl propanoate, methyl butanoat, methyl pentanoate, methyl hexanoate, methyl octanoate, methyl decanoate, methyl laurate, methyl dodecanoate, ethyl acetate, ethyl propanoate, ethyl butanoate, ethyl pentanoate, ethyl hexanoate, dimethyl oxalate, dimethyl malonate, dimethyl succinate, dimethyl glutarate, dimethyl adipate, diethyl oxalate, diethyl malonate, diethyl succinate, diethyl glutarate, diethyl adipate, dimethyl methylsuccinate, dimethyl 3-methylglutarate, methyl glycolate, ethyl glycolate, butyl glycolate, benzyl glycolate, methyl lactate, ethyl lactate, butyl lactate, tert-butyl lactate, ethyl 3-hydroxybutyrate, ethyl mandelate, dimethyl malate, diethyl malate, diisopropyl malate, dimethyl tartrate, diethyl tartrate, diisopropyl tartrate, trimethyl citrate, triethyl citrate, ethylene carbonate, propylene carbonate, trimethylene carbonate, diethyl carbonate, diphenyl carbonate, dimethyl dicarbonate, diethyl dicarbonate or di(tert-butyl) dicarbonate, in any one of the isomeric forms thereof.

When the aromatic compound comprises at least one ester function, step iI) is preferably carried out before step i), or steps I) and ii) are carried out at the same time. When the organic compound is a carboxylic acid cyclic ester, steps i) and ii) are more preferentially carried out at the same time.

All the embodiments relating to the nature of said organic compound can be combined together so that step ii) may be carried out by bringing said support into contact with at least one solution containing at least one organic compound comprising at least one ester function, in particular an organic compound comprising at least one ester function as cited above.

D) Organic Compound Comprising at Least One Amide Function

In another embodiment according to the invention, the organic compound comprises at least one amide function chosen from an acyclic amide function or a cyclic amide function optionally comprising alkyl substituents, aryl substituents or alkyl substituents containing unsaturations. The amide functions can be chosen from primary, secondary or tertiary amides.

The molar ratio of said organic compound comprising at least one amide function introduced during step ii) with respect to the element nickel introduced in step i) is between 0.01 and 1.5 mol/mol, preferably between 0.05 and 1.0 mol/mol, more preferentially between 0.08 and 0.9 mol/mol.

According to a first alternative form, the organic compound comprises at least one acyclic amide function.

Said organic compound may comprise a single amide function and does not contain another functional group, such as formamide, N-methylformamide, N,N-dimethylformamide, N-ethylformamide, N,N-diethylformamide, N,N-dibutylformamide, N,N-diisopropylformamide, N,N-diphenylformamide, acetamide, N-methylacetamide, N,N-dimethylmethanamide, N,N-diethylacetamide, N,N-dimethylpropionamide, propanamide, N-ethyl-N-methylpropanamide, benzamide or acetanilide, according to any one of the isomeric forms thereof. Preferably, said organic compound is chosen from formamide, N-methylformamide, N,N-dimethylformamide, N-ethylformamide, N,N-diethylformamide, acetamide, N-methylacetamide, N,N-dimethylmethanamide, N,N-diethylacetamide, N,N-dimethylpropionamide or propanamide.

Said organic compound may comprise two amide functions and does not contain another functional group, such as tetraacetylethylenediamine.

According to a second alternative form, the organic compound comprises at least one cyclic amide function, such as 1-formylpyrrolidine or 1-formylpiperidine, or a lactam function.

Preferably, said organic compound is chosen from β-lactam, γ-lactam, δ-lactam and ε-lactam and the derivatives thereof, according to any one of the isomeric forms thereof. More preferably, said organic compound is chosen from 2-pyrrolidone, N-methyl-2-pyrrolidone, γ-lactam or caprolactam, according to any one of the isomeric forms thereof.

According to a third alternative form, said organic compound may comprise at least one amide function and at least one other function other than the amide function. Preferably, said organic compound comprises at least one amide function and at least one carboxylic acid function, such as acetylleucine, N-acetylaspartic acid, aminohippuric acid, N-acetylglutamic acid or 4-acetamidobenzoic acid, according to any one of the isomeric forms thereof.

Preferably, said organic compound comprises at least one amide function and at least one alcohol function, such as glycolamide, lactamide, N,N-diethyl-2-hydroxyacetamide, 2-hydroxy-N-methylacetamide, 3-hydroxypropionamide, mandelamide, acetohydroxamic acid, butyrylhydroxamic acid or bucetin, according to any one of the isomeric forms thereof. Preferably, said organic compound is chosen from lactamide and glycolamide.

According to a fourth alternative form, the organic compound comprises at least one amide function and at least one additional nitrogen heteroatom, preferably chosen from urea, N-methylurea, N,N'-dimethylurea, 1,1-dimethylurea or tetramethylurea, according to any one of the isomeric forms thereof.

Among all the organic compounds comprising at least one amide function above, preference is more particularly given to formamide, N-methylformamide, N,N-dimethylformamide, N-ethylformamide, N,N-diethylformamide, acetamide, N-methylacetamide, N,N-dimethylmethanamide, N,N-diethylacetamide, N,N-dimethylpropionamide, propanamide, 2-pyrrolidone, N-methyl-2-pyrrolidone, γ-lactam, caprolactam, acetylleucine, N-acetylaspartic acid, aminohippuric acid, N-acetylglutamic acid, 4-acetamidobenzoic acid, lactamide and glycolamide, urea, N-methylurea, N,N'-dimethylurea, 1,1-dimethylurea or tetramethylurea, according to any one of the isomeric forms thereof.

Preferably, when said organic compound comprises at least one acyclic amide function, step i) is carried out before step ii) or step ii) is carried out before step i). Preferentially, step i) is carried out before step ii).

Preferably, when said organic compound comprises at least one cyclic amide function or a lactam function, step ii) is carried out before step i), or steps i) and ii) are carried out at the same time.

Preferably, when said organic compound comprises at least one amide function and at least one other function other from the amide function, and in particular a carboxylic acid function, or an alcohol function, or an additional nitrogen heteroatom, step i) is carried out before step ii) or steps i) and ii) are carried out at the same time. Preferentially, step i) is carried out before step ii).

All the embodiments relating to the nature of said organic compound can be combined together so that step ii) may be carried out by bringing said support into contact with one or more solutions containing one or more organic compounds comprising at least one amide function, in particular one or more organic compounds comprising at least one amide function as cited above.

Implementation of Steps i) and ii)

The process for the preparation of the nickel catalyst comprises several embodiments. They differ in particular in the order of introduction of the organic compound and of the nickel precursor, it being possible for the organic compound to be brought into contact with the support either after the nickel precursor is brought into contact with the support, or before the nickel precursor is brought into contact with the support, or at the same time as the nickel is bought into contact with the support.

A first embodiment consists in carrying out said step i) prior to said step ii).

A second embodiment consists in carrying out said step ii) prior to said step i).

Each step i) and ii) of bringing the support into contact with the nickel precursor (step i) and of bringing the support into contact with at least one solution containing at least one organic compound comprising at least one carboxylic acid function, or at least one alcohol function, or at least one ester function, or at least one amide function, (step ii), is carried out at least once and may advantageously be carried out several times, optionally in the presence of a nickel precursor and/or of an organic compound which is(are) identical or different in each step i) and/or ii) respectively, all the possible combinations for carrying out steps i) and ii) coming within the scope of the invention.

A third embodiment consists in carrying out said step i) and said step ii) simultaneously (co-contacting). This embodiment may advantageously comprise the implementation of one or more steps i), optionally with an identical or different nickel precursor in each step i). In particular, one or more steps i) proceed and/or advantageously follow said co-contacting step, optionally with an identical or different nickel precursor in each step. This embodiment may also comprise several co-contacting steps: steps i) and ii) are carried out simultaneously several times, optionally in the presence of a nickel precursor and/or of an organic compound which is(are) identical or different in each co-contacting step.

Each contacting step may preferably be followed by an intermediate drying step. The intermediate drying step is carried out at a temperature below 250° C., preferably of between 15 and 240° C., more preferably between 30 and 220° C., more preferably still between 50 and 200° C. and in an even more preferred way between 70 and 180° C. Advantageously, when an intermediate drying step is carried out, an intermediate calcining step may be carried out. The intermediate calcining step is carried out at a temperature of between 250 and 1000° C., preferably between 250 et 750° C.

Advantageously, after each contacting step, whether this is a step of bringing the nickel precursor into contact with the support, a step of bringing the organic compound into contact with the support, or a step of bringing the nickel precursor and the organic compound into contact simultaneously with the support, it is possible to leave the impregnated support to mature, optionally before an intermediate drying step. Maturing allows the solution to be distributed homogeneously within the support. When a maturing step is carried out, said step is advantageously carried out at atmospheric pressure or at reduced pressure, under an inert atmosphere or under an oxygen-containing atmosphere or under a water-containing atmosphere, and at a temperature of between 10° C. and 50° C. and preferably at ambient temperature. Generally, a maturing time of less than forty-eight hours and preferably of between five minutes and five hours is sufficient. Longer periods of time are not ruled out but do not necessarily contribute an improvement.

Step iii)—Drying

In accordance with the drying step iii) of the implementation for the preparation of the catalyst, prepared according to at least one mode of implementation described above, the drying step is carried out at a temperature below 250° C., advantageously between 15 and 240° C., preferably between 30 and 220° C., more preferentially still between 50 and 200° C., and even more preferentially between 70 and 180° C., for a period typically of between 10 minutes and 24 hours. Longer periods of time are not ruled out but do not necessarily contribute an improvement.

The drying stage can be carried out by any technique known to a person skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air or nitrogen.

Step iv)—Calcining (Optional)

Optionally, on conclusion of the drying step iii), a calcining step iv) is carried out at a temperature of between 250° C. and 1000° C., preferably of between 250° C. and 750° C., under an inert atmosphere or under an oxygen-containing atmosphere. The duration of this heat treatment is generally between 15 minutes and 10 hours. Longer periods of time are not ruled out but do not necessarily contribute an improvement. After this treatment, the nickel of the active phase is thus in oxide form and the catalyst contains no more or very little organic compound introduced during the synthesis thereof.

Step v)—Reducing Treatment (Optional)

Prior to the use of the catalyst in the catalytic reactor and the implementation of a hydrogenation process, at least one reducing treatment step v) is advantageously carried out in the presence of a reducing gas after steps iii) or iv), so as to obtain a catalyst comprising nickel at least partially in the metallic form.

This treatment makes it possible to activate said catalyst and to form metallic particles, in particular of nickel in the zero-valent state. Said reducing treatment may be carried out in situ or ex situ, that is to say after or before the catalyst is charged to the hydrogenation reactor. Said reducing treatment step v) may be carried out on the catalyst that has optionally been subjected to the passivation step vi), described hereinafter.

The reducing gas is preferably hydrogen. The hydrogen can be used pure or as a mixture (for example a hydrogen/nitrogen or hydrogen/argon or hydrogen/methane mixture). In the case where the hydrogen is used as a mixture, all the proportions can be envisaged.

Said reducing treatment is carried out at a temperature of between 120 and 500° C., preferably between 150 and 450° C. When the catalyst is not subjected to passivation or is subjected to a reducing treatment before passivation, the reducing treatment is carried out at a temperature of between 180 and 500° C., preferably between 200 and 450° C., and more preferentially still between 350 and 450° C. When the catalyst has been subjected beforehand to a passivation, the reducing treatment is generally carried out at a temperature of between 120 and 350° C., preferably between 150 and 350° C.

The duration of the reducing treatment is generally between 2 and 40 hours, preferably between 3 and 30 hours. The rise in temperature up to the desired reduction temperature is generally slow, for example set between 0.1 and 10° C./min, preferably between 0.3 and 7° C./min.

The hydrogen flow rate, expressed in l/hour/gram of catalyst, is between 0.01 and 100 l/hour/gram of catalyst, preferably between 0.05 and 10 l/hour/gram of catalyst and more preferably still between 0.1 and 5 l/hour/gram of catalyst.

Step vi)—Passivation (Optional)

Prior to the use thereof in the catalytic reactor, the catalyst according to the invention may optionally be subjected to a step of passivation (step vi) by an oxygen compound or by $CO_2$, before or after the reducing treatment step v). This passivation step may be carried out ex situ. The passivation step is carried out by the use of methods known to a person skilled in the art.

The step of passivation by an oxygen compound or by $CO_2$ is generally carried out after a reducing treatment beforehand at high temperature, generally of between 350 and 500° C., and makes it possible to preserve the metallic phase of the catalyst in the presence of air. A second reducing treatment at lower temperature, generally between 120 and 350° C., is subsequently generally carried out. The oxygen compound is generally air or any other oxygen-containing stream.

The catalyst prepared according to at least any one of the embodiments described above, optionally in combination with said step iv) and/or said step v) and/or said step vi) is, before the implementation of the hydrogenation process according to the invention, either completely or at least partially stripped of said organic compound. The introduction of the organic compound comprising at least one carboxylic acid function, or at least one alcohol function, or at least one ester function, or at least one amide function, during the preparation thereof has made it possible to increase the dispersion of the active phase thus leading to a more active and/or more selective catalyst.

The invention is illustrated by the examples which follow.

All of the catalysts prepared in examples 2 to 10 are prepared with the same content of element nickel. The support used for the preparation of each of these catalysts is a δ-alumina having a pore volume of 0.67 ml/g and a BET surface area equal to 140 m²/g.

Example 1: Preparation of the Aqueous Solutions of Ni Precursors

A first aqueous solution of Ni precursors (solution S1) used for the preparation of the catalysts A, B, C, D, G and H is prepared at 25° C. by dissolving 276 g of nickel nitrate $Ni(NO_3)_2 \cdot 6H_2O$ (supplied by Strem Chemicals®) in a volume of 100 ml of demineralized water. The solution S1, the NiO concentration of which is 19.0% by weight (relative to the mass of the solution), is obtained.

A second aqueous solution of Ni precursors (solution S2) used for the preparation of the catalysts E and I is prepared at 25° C. by dissolving 151 g of nickel nitrate $Ni(NO_3)_2 \cdot 6H_2O$ (supplied by Strem Chemicals®) in a volume of 50 ml of demineralized water. The solution S2, the NiO concentration of which is 19.3% by weight (relative to the mass of the solution), is obtained.

Example 2 (Comparative): Preparation of a Catalyst a by Impregnation of Nickel Nitrate without Additive The solution S1 prepared in example 1 is dry-impregnated on 10 g of said alumina support. The solid thus obtained is subsequently dried in an oven overnight at 120° C., and then calcined under a stream of air of 1 l/h/g of catalyst at 450° C. for 2 hours.

The calcined catalyst A thus prepared contains 13.8% by weight of the element nickel supported on alumina and it has nickel oxide crystallites, the mean diameter of which (determined by X-ray diffraction from the width of the diffraction line located at the angle 2θ=43°) is 15.2 nm.

Example 3 (Invention): Preparation of a Catalyst B by Successive Impregnation of Nickel Nitrate then of 2-Hydroxypropanoic Acid (Lactic Acid)

The catalyst B is prepared by impregnation of Ni nitrate on said alumina support, then by impregnation of lactic acid using a {lactic acid/nickel} molar ratio equal to 0.6.

In order to do this, the solution S1 prepared in example 1 is dry-impregnated on said alumina support. The solid B1 thus obtained is then dried in an oven overnight at 120° C. Next, an aqueous solution B' is prepared by dissolving 4.19 g of lactic acid (CAS 15-21-5, supplied by Fluka®) in 20 ml of demineralized water. This solution B' is then dry-impregnated on 10 g of the previously prepared solid B1. The solid thus obtained is subsequently dried in an oven overnight at 120° C., and then calcined under a stream of air of 1 l/h/g of catalyst at 450° C. for 2 hours.

The calcined catalyst B thus prepared contains 13.8% by weight of the element nickel supported on alumina and it has nickel oxide crystallites, the mean diameter of which is 5.1 nm.

Example 4 (Invention): Preparation of a Catalyst C by Successive Impregnation of Nickel Nitrate then of 2-Hydroxypropanoic Acid (Lactic Acid), with an Additive-to-Nickel Molar Ratio of 0.08

The catalyst C is prepared by impregnation of Ni nitrate on said alumina support, then by impregnation of lactic acid using a {lactic acid/nickel} molar ratio equal to 0.08.

In order to do this, the solution S1 prepared in example 1 is dry-impregnated on said alumina support. The solid C1 thus obtained is then dried in an oven overnight at 120° C. Next, an aqueous solution C' is prepared by dissolving 0.56 g of lactic acid (CAS 15-21-5, supplied by Fluka®) in 20 ml of demineralized water. This solution C' is then dry-impregnated on 10 g of the previously prepared solid C1. The solid thus obtained is subsequently dried in an oven overnight at 120° C., and then calcined under a stream of air of 1 l/h/g of catalyst at 450° C. for 2 hours.

The calcined catalyst C thus prepared contains 13.8% by weight of the element nickel supported on alumina and it has nickel oxide crystallites, the mean diameter of which is 7.2 nm.

Example 5 (Invention): Preparation of a Catalyst D by Successive Impregnation of Nickel Nitrate then of 2-Hydroxypropanoic Acid (Lactic Acid), with an Additive-to-Nickel Molar Ratio of 0.9

The catalyst D is prepared by impregnation of Ni nitrate on said alumina support, then by impregnation of lactic acid using a {lactic acid/nickel} molar ratio equal to 0.9.

In order to do this, the solution S1 prepared in example 1 is dry-impregnated on said alumina support. The solid D1 thus obtained is then dried in an oven overnight at 120° C. Next, an aqueous solution D' is prepared by dissolving 6.29 g of lactic acid (CAS 15-21-5, supplied by Fluka®) in 20 ml of demineralized water. This solution D' is then dry-impregnated on 10 g of the previously prepared solid D1. The solid thus obtained is subsequently dried in an oven overnight at 120° C., and then calcined under a stream of air of 1 l/h/g of catalyst at 450° C. for 2 hours.

The calcined catalyst D thus prepared contains 13.8% by weight of the element nickel supported on alumina and it has nickel oxide crystallites, the mean diameter of which is 4.9 nm.

Example 6 (Invention): Preparation of a Catalyst E by Successive Impregnation of (D)-(+)-Mannose then of Nickel Nitrate The catalyst E is prepared by impregnation of (D)-(+)-mannose on said alumina support, then by impregnation of Ni nitrate using a {(D)-(+)-mannose/nickel} molar ratio equal to 0.6.

In order to do this, an aqueous solution E' is prepared by dissolving 6.20 g of (D)-(+)-mannose (CAS 3458-28-4, supplied by Sigma-Aldrich®, 99% purity) in 20 ml of demineralized water. This solution E' is then dry-impregnated on said alumina support. The solid E1 thus obtained is subsequently dried in an oven overnight at 120° C. The solution S2 prepared in example 1 is dry-impregnated on 10 g of the previously prepared solid E1. The solid thus obtained is subsequently dried in an oven overnight at 120° C., and then calcined under a stream of air of 1 l/h/g of catalyst at 450° C. for 2 hours.

The calcined catalyst E thus prepared contains 13.8% by weight of the element nickel supported on alumina and it has nickel oxide crystallites, the mean diameter of which is 4.8 nm.

Example 7 (Invention): Preparation of a Catalyst F by Co-Impregnation of Nickel Nitrate and of (D)-(+)-Mannose The catalyst F is prepared by co-impregnation of nickel nitrate and of (D)-(+)-mannose on said alumina support using a {(D)-(+)-mannose/nickel} molar ratio equal to 0.6.

In order to do this, an aqueous solution F' is prepared by dissolving 62.0 g of nickel nitrate $Ni(NO_3)_2.6H_2O$ (supplied by Strem Chemicals®) and 23.0 g of (D)-(+)-mannose (CAS 3458-28-4, supplied by Sigma-Aldrich®, 99% purity) in 20 ml of demineralized water. This solution F' is then dry-impregnated on 10 g of said alumina support. The solid thus obtained is subsequently dried in an oven overnight at 120° C., and then calcined under a stream of air of 1 l/h/g of catalyst at 450° C. for 2 hours.

The calcined catalyst F thus prepared contains 13.8% by weight of the element nickel supported on alumina and it has nickel oxide crystallites, the mean diameter of which is 6.3 nm.

Example 8 (Invention): Preparation of a Catalyst G by Successive Impregnation of Nickel Nitrate then of Dimethyl Malate The catalyst G is prepared by impregnation of Ni nitrate on said alumina support, then by impregnation of dimethyl malate using a {dimethyl malate/nickel} molar ratio equal to 0.6.

In order to do this, the solution S1 prepared in example 1 is dry-impregnated on said alumina support. The solid G1 thus obtained is then dried in an oven overnight at 120° C. Next, an aqueous solution G' is prepared by dissolving 7.50 g of dimethyl malate (CAS 1587-15-1, supplied by Sigma-Aldrich®) in 20 ml of demineralized water. This solution G' is then dry-impregnated on 10 g of the previously prepared solid G1. The solid thus obtained is subsequently dried in an oven overnight at 120° C., and then calcined under a stream of air of 1 l/h/g of catalyst at 450° C. for 2 hours.

The calcined catalyst G thus prepared contains 13.8% by weight of the element nickel supported on alumina and it has nickel oxide crystallites, the mean diameter of which is 5.7 nm.

Example 9 (Invention): Preparation of a Catalyst H by Successive Impregnation of Nickel Nitrate then of Dimethyl Malate, without Final Calcining The catalyst H is prepared by impregnation of Ni nitrate on said alumina support, then by impregnation of dimethyl malate using a {dimethyl malate/nickel} molar ratio equal to 0.6.

In order to do this, the solution S1 prepared in example 1 is dry-impregnated on said alumina support. The solid H1 thus obtained is then dried in an oven overnight at 120° C. Next, an aqueous solution H' is prepared by dissolving 7.50 g of dimethyl malate (CAS 1587-15-1, supplied by Sigma-Aldrich®) in 20 ml of demineralized water. This solution H' is then dry-impregnated on 10 g of the previously prepared solid H1. The solid thus obtained is then dried in an oven overnight at 120° C., without any heat treatment. The catalyst H is obtained.

In order to carry out the characterizations, a portion of this catalyst H is calcined under a stream of air of 1 l/h/g of catalyst at 450° C. for 2 hours, in order to obtain the calcined catalyst H_calci. The calcined catalyst H_calci contains 13.8% by weight of the element nickel supported on alumina and it has nickel oxide crystallites, the mean diameter of which is 5.9 nm.

Example 10 (Invention): Preparation of a Catalyst I by Successive Impregnation of γ-Lactam then of Nickel Nitrate The catalyst I is prepared by impregnation of γ-lactam on said alumina support, then by impregnation of Ni nitrate using a {γ-lactam/nickel} molar ratio equal to 0.6.

In order to do this, an aqueous solution I' is prepared by dissolving 3.94 g of γ-lactam (CAS 616-45-5, supplied by Sigma-Aldrich®) in 20 ml of demineralized water. This solution I' is then dry-impregnated on said alumina support. The solid 11 thus obtained is subsequently dried in an oven overnight at 120° C. The solution S2 prepared in example 1 is dry-impregnated on 10 g of the previously prepared solid 11. The solid thus obtained is subsequently dried in an oven overnight at 120° C., and then calcined under a stream of air of 1 l/h/g of catalyst at 450° C. for 2 hours.

The calcined catalyst I thus prepared contains 13.8% by weight of the element nickel supported on alumina and it has nickel oxide crystallites, the mean diameter of which is 5.2 nm.

Example 11: Evaluation of the Catalytic Properties of the Catalysts a to I in the Hydrogenation of Toluene The catalysts A to I described in the above examples are also tested with regard to the reaction for the hydrogenation of toluene.

The selective hydrogenation reaction is carried out in a 500 ml stainless steel autoclave which is provided with a magnetically-driven mechanical stirrer and which is able to operate under a maximum pressure of 100 bar (10 MPa) and temperatures of between 5° C. and 200° C.

Prior to its introduction into the autoclave, an amount of 2 ml of catalyst is reduced ex situ under a stream of hydrogen of 1 l/h/g of catalyst at 400° C. for 16 hours (temperature rise gradient of 1° C./min) and then it is transferred into the autoclave, with the exclusion of air. After addition of 216 ml of n-heptane (supplied by VWR®, purity>99% Chromanorm HPLC), the autoclave is closed, purged, then pressurized under 35 bar (3.5 MPa) of hydrogen and brought to the temperature of the test, which is equal to 80° C. At the time t=0, approximately 26 g of toluene (supplied by SDS®, purity>99.8%) are introduced into the autoclave (the initial composition of the reaction mixture is then toluene 6% by weight/n-heptane 94% by weight) and stirring is started at 1600 rev/min. The pressure is kept constant at 35 bar (3.5 MPa) in the autoclave using a storage cylinder located upstream of the reactor.

The progress of the reaction is monitored by taking samples from the reaction medium at regular time intervals: the toluene is completely hydrogenated to give methylcyclohexane. The hydrogen consumption is also monitored over time by the decrease in pressure in a storage cylinder located upstream of the reactor. The catalytic activity is expressed in moles of $H_2$ consumed per minute and per gram of Ni.

The catalytic activities measured for the catalysts A to I are given in table 1 below. They are with reference to the catalytic activity measured for the catalyst A ($A_{HYD1}$).

TABLE 1

Comparison of the performance in the hydrogenation of toluene

| Catalyst | Additive used | Method of introducing the additive | Mean size of the NiO crystallites (nm) | $A_{HYD1}$ (%) |
|---|---|---|---|---|
| A (not in accordance) | — | — | 15.2 | 100 |
| B (in accordance) | Lactic acid | Steps i) then ii) | 5.1 | 296 |
| C (in accordance) | Lactic acid | Steps i) then ii) - additive/Ni molar ratio = 0.08 | 7.2 | 205 |
| D (in accordance) | Lactic acid | Steps i) then ii) - additive/Ni molar ratio = 0.9 | 4.9 | 310 |
| E (in accordance) | Mannose | Steps ii) then i) | 4.8 | 317 |
| F (in accordance) | Mannose | Steps ii) and i) simultaneously | 6.3 | 243 |
| G (in accordance) | Dimethyl malate | Steps i) then ii) | 5.7 | 266 |
| H (in accordance) | Dimethyl malate | Steps i) then ii) - without calcining | 5.9 | 257 |
| I (in accordance) | γ-lactam | Steps ii) then i) | 5.2 | 292 |

The results that appear in table 1 demonstrate that the catalysts B to I, prepared in the presence of an organic compound (having at least one carboxylic acid function, or at least one alcohol function, or at least one ester function, or at least one amide function), are more active than the catalyst A prepared in the absence of this type of organic compound. This effect is related to the decrease in the size of the Ni particles.

The invention claimed is:

1. A process comprising hydrogenation of at least one aromatic or polyaromatic compound contained in a hydrocarbon feedstock having a final boiling point below or equal to 650° C., said process being carried out in gas phase or in liquid phase, at a temperature of 30 to 350° C., at a pressure of 0.1 to 20 MPa, at a hydrogen/(aromatic compounds to be hydrogenated) molar ratio of 0.1 to 10 and at an hourly space velocity HSV of 0.05 to 50 h$^{-1}$, in the presence of a catalyst comprising an alumina support and an active phase comprising nickel, said active phase not comprising a metal from Group VIB, said process comprising:
 a) first preparing said catalyst by at least:
  i) bringing said alumina support into contact with at least one solution containing at least one nickel precursor,
  ii) bringing said alumina support into contact with at least one solution containing at least one organic compound comprising at least one carboxylic acid functional group;
  whereby after i) and ii) an impregnated support is produced,
  iii) drying said impregnated support at a temperature below 180° C.;
  i) and ii) being carried out separately, in any order, or at the same time, with the proviso that the catalyst is not calcined under a calcination temperature range of 250° C.-1000° C., thereby producing an uncalcined catalyst, and b) hydrogenating the at least one aromatic or polyaromatic compound contained in the hydrocarbon feedstock with the uncalcined catalyst.

2. The process as claimed in claim 1, wherein i) and ii) are carried out at the same time.

3. The process as claimed in claim 1, wherein i) is carried out before ii).

4. The process as claimed in claim 1 wherein ii) is carried out before i).

5. The process as claimed in claim 1, wherein i) and/or ii) is (are) carried out by dry impregnation.

6. The process as claimed in claim 1, wherein a content of element nickel is 8 to 65% by weight relative to a total weight of the catalyst.

7. The process as claimed in claim 1, wherein said organic compound is at least one monocarboxylic acid, dicarboxylic acid, tricarboxylic acid or tetracarboxylic acid.

8. The process as claimed in claim 1, wherein said organic compound further comprises at least one alcohol functional group.

9. The process as claimed in claim 8, wherein said organic compound further comprises:
   organic compounds having a single alcohol functional group;
   organic compounds having two alcohol functional groups;
   diethylene glycol, triethylene glycol, tetraethylene glycol or a polyethylene glycol corresponding to the formula $H(OC_2H_4)_nOH$ with n greater than 4 and having an average molar mass of less than 20 000 g/mol;
   monosaccharides of empirical formula $C_n(H_2O)_n$ with n between 3 and 12; or
   disaccharides, trisaccharides, or monosaccharide derivatives.

10. The process as claimed in claim 1, wherein said organic compound further comprises at least one ester functional group.

11. The process as claimed in claim 10, wherein said organic compound further comprises:
   carboxylic acid linear or cyclic or unsaturated cyclic esters;
   organic compounds having at least two carboxylic acid ester functional groups;
   organic compounds having at least one carboxylic acid ester functional group and at least one second functional group from alcohols, ethers, ketones or aldehydes;
   carbonic acid cyclic or linear esters; or
   carbonic acid linear diesters.

12. The process as claimed in claim 1, wherein said organic compound further comprises at least one amide functional group.

13. The process as claimed in claim 12, wherein said organic compound further comprises:
   acyclic amides having one or two amide functional groups;
   cyclic amides or lactams;
   organic compounds having at least one amide functional group and a carboxylic acid functional group or an alcohol functional group; or
   organic compounds having at least one amide functional group and an additional nitrogen heteroatom.

14. The process as claimed in claim 1, comprising an aromatic hydrogenation of benzene at a temperature of 30 to 250° C., at a pressure of 0.1 to 10 MPa, at a hydrogen/(benzene) molar ratio of 0.1 to 10 and at an hourly space velocity HSV of 0.05 to 50 $h^{-1}$.

* * * * *